United States Patent
Seyama et al.

(10) Patent No.: US 11,940,333 B2
(45) Date of Patent: Mar. 26, 2024

(54) LIVING BODY INTERNAL TEMPERATURE MEASURING DEVICE AND LIVING BODY INTERNAL TEMPERATURE MEASURING METHOD

(71) Applicant: Nippon Telegraph and Telephone Corporation, Tokyo (JP)

(72) Inventors: Michiko Seyama, Tokyo (JP); Daichi Matsunaga, Tokyo (JP); Yujiro Tanaka, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 553 days.

(21) Appl. No.: 17/058,555

(22) PCT Filed: May 14, 2019

(86) PCT No.: PCT/JP2019/019125
§ 371 (c)(1),
(2) Date: Nov. 24, 2020

(87) PCT Pub. No.: WO2019/230370
PCT Pub. Date: Dec. 5, 2019

(65) Prior Publication Data
US 2021/0123819 A1    Apr. 29, 2021

(30) Foreign Application Priority Data

May 28, 2018    (JP) .................................. 2018-101586

(51) Int. Cl.
*G01K 13/20*    (2021.01)
*A61B 5/01*    (2006.01)
(Continued)

(52) U.S. Cl.
CPC ................. *G01K 13/20* (2021.01); *A61B 5/01* (2013.01); *A61B 5/026* (2013.01); *G01K 7/42* (2013.01);
(Continued)

(58) Field of Classification Search
CPC .......... G01K 13/20; G01K 7/42; G01K 17/20; G01K 7/427; A61B 5/01; A61B 5/026;
(Continued)

(56) References Cited

U.S. PATENT DOCUMENTS

2015/0327779 A1* 11/2015 Breskin ................ A61B 8/0808
600/407

FOREIGN PATENT DOCUMENTS

| JP | 2017217224 A | * | 12/2017 | ............... A61B 5/01 |
| JP | 2018021833 A | * | 2/2018 | |
| WO | WO-2014097293 A1 | * | 6/2014 | ........... A61B 5/0095 |

OTHER PUBLICATIONS

Nakayama, et al., "Physiology of energy metabolism and thermoregulation," New Physiological Science System, 1987, pp. 96-97.
(Continued)

*Primary Examiner* — Manish S Shah
*Assistant Examiner* — Christian T Bryant
(74) *Attorney, Agent, or Firm* — Slater Matsil, LLP (57) ABSTRACT

A heat flux sensor including two temperature sensors is used to obtain time-series data of a core temperature of a living body, and a blood flow rate in a vicinity of the heat flux sensor is measured by a blood flow sensor. In an arithmetic circuit, a delay time until a fluctuation of the core temperature of the living body is reflected on an epidermis temperature is calculated on the basis of the blood flow rate measured by the blood flow sensor and a previously prepared relation between the blood flow rate and the delay time until the fluctuation of the core temperature of the living (Continued)

body is reflected on the epidermis temperature, and a time corresponding to the core temperature of the living body on the basis of the delay time is corrected.

13 Claims, 9 Drawing Sheets

(51) Int. Cl.
*A61B 5/026* (2006.01)
*A61B 8/06* (2006.01)
*G01K 7/42* (2006.01)
*G01K 17/20* (2006.01)
*G01J 5/00* (2022.01)

(52) U.S. Cl.
CPC ............ *G01K 17/20* (2013.01); *A61B 5/0261* (2013.01); *A61B 8/06* (2013.01); *G01J 5/0025* (2013.01); *G01K 7/427* (2013.01)

(58) Field of Classification Search
CPC ......... A61B 5/0261; A61B 8/06; A61B 5/015; G01J 5/0025
USPC ......................................................... 374/100
See application file for complete search history.

(56) References Cited

OTHER PUBLICATIONS

Nakagawa et al., "Proposal of Wearable Deep Thermometer with MEMS Thermal Flow Easting Sensor," Journal of the Institute of Electrical Engineers E (Sensor Micro machine Division Magazine), vol. 135, No. 8, 2015, pp. 343-348.

* cited by examiner

LIVING BODY INTERNAL TEMPERATURE MEASURING DEVICE AND LIVING BODY INTERNAL TEMPERATURE MEASURING METHOD

CROSS-REFERENCE TO RELATED APPLICATIONS

This application is a national phase entry of PCT Application No. PCT/JP2019/019125, filed on May 14, 2019, which claims priority to Japanese Application No. 2018-101586, filed on May 28, 2018, which applications are hereby incorporated herein by reference.

TECHNICAL FIELD

The present invention relates to an internal body temperature measurement device and an internal body temperature measurement method for measuring a temperature of a core part of a living body.

BACKGROUND

A living body has a temperature region which is not affected by a change in an outside air temperature or the like beyond a certain depth from an epidermis toward a core part (hereinafter, the temperature of the region is referred to as a "core temperature" or a "deep body temperature"). It is known that measuring a fluctuation of the core temperature is useful for grasping an internal body rhythm.

In order to measure the core temperature, a percutaneous temperature measurement method rather than an invasive measurement such as indwelling is easy and useful for routine body temperature management.

CITATION LIST

Non-Patent Literature

Non-Patent Literature 1: Akio Nakayama, "Handbook of physiological sciences: Volume 22", Igaku-Shoin (1987)
Non-Patent Literature 2: Shinya Nakagawa et al., "Wearable Core Temperature Thermometer Implemented by the MEMS Heat Flux Sensor", IEEJ Transactions on Electronics, Vol. 135 (2015) No. 8, P. 343-348.

SUMMARY

Technical Problem

However, in a conventional percutaneous body temperature measurement device, it is difficult to accurately grasp the fluctuation of the core temperature. One of the causes is a fluctuation of the time until the fluctuation of the core temperature is reflected in a temperature measured on the epidermis, that is, a fluctuation of a delay time.

Figure 15:
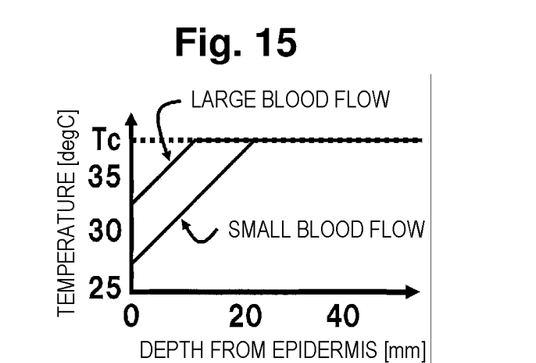
FIG. 15 is a diagram illustrating a relation between the depth from the epidermis to the temperature region of the core temperature and the blood flow rate.

As illustrated in FIG. 15, it is known that the depth from the epidermis to the temperature region of the core temperature Tc depends on a blood flow rate (Non-Patent Literature 1, FIG. 59). The blood flow of a body surface increases when blood vessel presents present in a dermis layer and called arteriovenous anastomoses (AVA) is dilated by a neural activity of the body. When the blood flow rate of the body surface increases, the heat energy of the core part moves together with the blood flow to a surface layer, and thus the apparent depth from the epidermis to the temperature region of the core temperature becomes shallow.

When a blood flow rate in a body surface changes from time to time, an apparent depth from the epidermis to the temperature region of the core temperature changes, and a delay time until the fluctuation in core temperature is reflected in the temperature measured on the epidermis also fluctuates. Therefore, it is not known what time a core temperature value reflected in a percutaneously measured value is actually measured, and as a result, it is not possible to accurately grasp the fluctuation of the core temperature.

In this regard, an object of embodiments of the present invention is to provide an internal body temperature measurement device capable of more accurately grasping a fluctuation in core temperature.

Means for Solving the Problem

In order to achieve the above-described object, an internal body temperature measurement device according to embodiments of the present invention includes: a temperature sensor (20s) which measures an epidermis temperature of a living body; a heat flux sensor (20) which measures a magnitude of a heat flux discharged from a body surface of the living body; a blood flow sensor (30) which measures a blood flow rate in a vicinity of the heat flux sensor; a storage unit (50) which stores a relation between the blood flow rate in the vicinity of the heat flux sensor and a parameter regarding a delay time until a fluctuation of a core temperature of the living body is reflected on the epidermis temperature; and an arithmetic circuit (40) configured to calculate the core temperature of the living body from the epidermis temperature measured by the temperature sensor and the magnitude of the heat flux measured by the heat flux sensor, calculate the delay time on a basis of the blood flow rate in the vicinity of the heat flux sensor and the relation stored in the storage unit, and correct a time corresponding to the core temperature of the living body on a basis of the delay time.

In the internal body temperature measurement device according to embodiments of the present invention, the arithmetic circuit (40) may include: a first calculation unit (41) which calculates the core temperature of the living body from the epidermis temperature measured by the temperature sensor and the magnitude of the heat flux measured by the heat flux sensor, a second calculation unit (43) which calculates the delay time on the basis of the blood flow rate in the vicinity of the heat flux sensor and the relation stored in the storage unit, and a correction unit (44) which corrects the time corresponding to the core temperature of the living body on the basis of the delay time.

In the internal body temperature measurement device according to embodiments of the present invention, the parameter may be a time constant of a fluctuation of the epidermis temperature with respect to the fluctuation of the core temperature of the living body or the delay time.

The internal body temperature measurement device according to embodiments of the present invention further includes at least two of the blood flow sensors (30-1 and 30-2), and the arithmetic circuit (40) may obtain a representative value of respective blood flow rates measured by the at least two blood flow sensors and obtains a value of the parameter corresponding to the representative value of the blood flow rates by using the relation.

An internal body temperature measurement method according to embodiments of the present invention includes: a step (S10) of measuring an epidermis temperature of a living body and a magnitude of a heat flux discharged from a body surface of the living body; a step (S20) of measuring a blood flow rate of the body surface; and steps (S40, S50, and S70) of calculating a core temperature of the living body from the measured epidermis temperature and the measured magnitude of the heat flux, calculating, on a basis of a previously prepared relation between the blood flow rate and a parameter regarding a delay time until a fluctuation of the core temperature of the living body is reflected on the epidermis temperature and the blood flow rate on the body surface, the delay time, and correcting a time corresponding to the core temperature of the living body on a basis of the delay time.

Effects of Embodiments of the Invention

According to embodiments of the present invention, it is possible to correct a time of time-series data of a core temperature based on a delay time calculated based on a blood flow rate of a body surface of a living body and thus to grasp a fluctuation of the core temperature more accurately.

DETAILED DESCRIPTION OF ILLUSTRATIVE EMBODIMENTS

Hereinafter, embodiments of the present invention will be described with reference to the drawings.

First Embodiment

Measurement Principle of Internal Body Temperature Measurement Device

Figure 1:
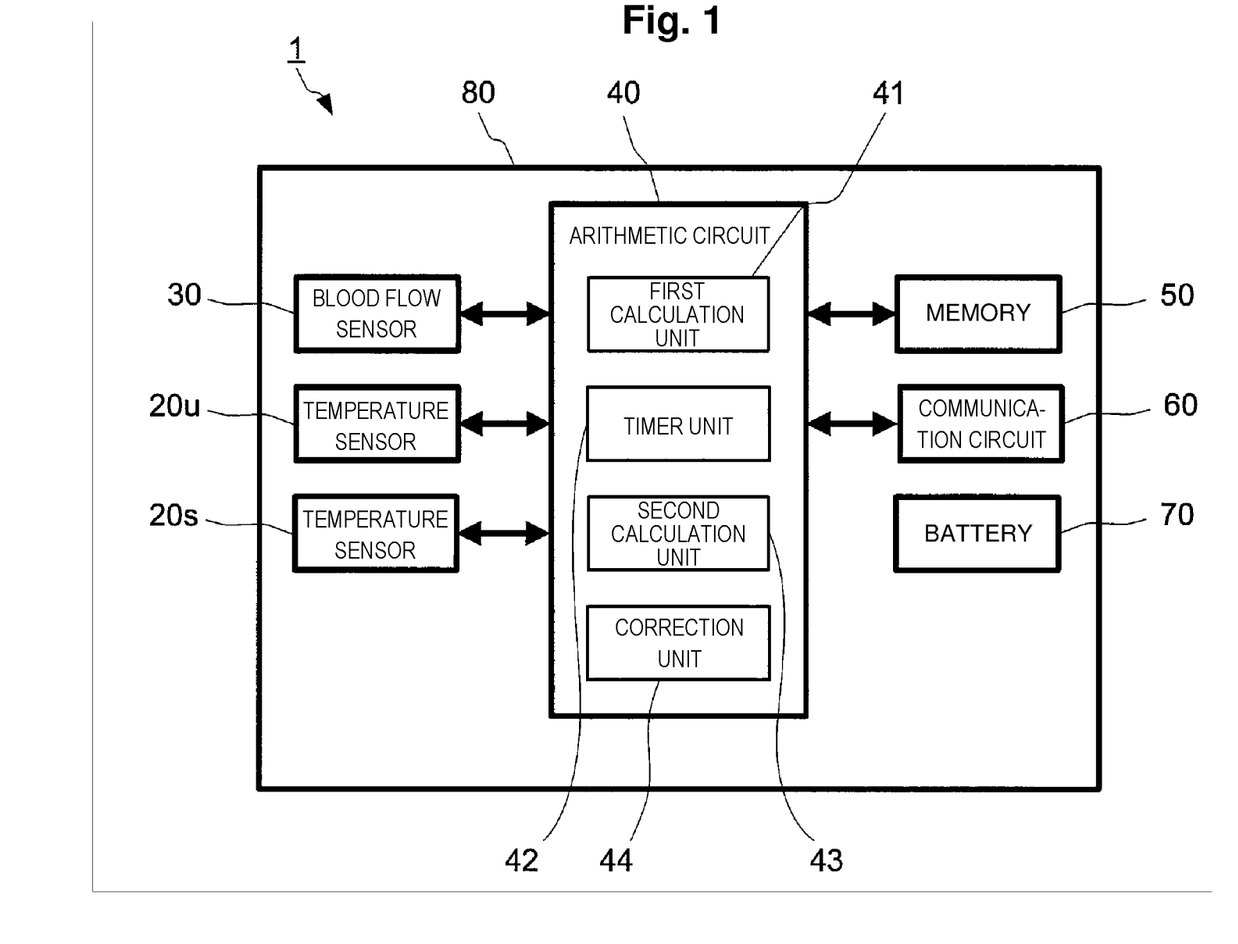
FIG. 1 is a diagram illustrating a configuration of an internal body temperature measurement device according to a first embodiment of the present invention.

As illustrated in FIG. 1, an internal body temperature measurement device 1 according to a first embodiment of the present invention includes, on a sheet-shaped base material 80, a heat flux sensor 20, a blood flow sensor 30, an arithmetic circuit 40, a memory 50, a communication circuit 60 which functions as an I/F circuit with an outside, and a battery 70 which supplies power to the arithmetic circuit 40, the communication circuit 60, or the like.

Figure 2:
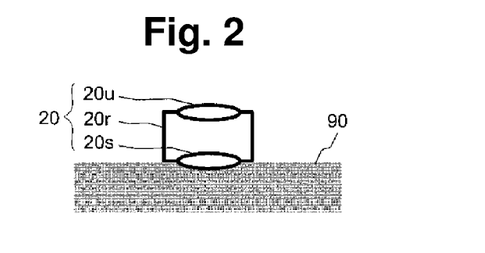
FIG. 2 is a diagram illustrating a configuration of a heat flux sensor including a temperature sensor.

Herein, the heat flux sensor 20 is a device which measures the movement of heat per unit time/unit area. As illustrated in FIG. 2, in this embodiment, the heat flux sensor 20 having a temperature sensor 20u and a temperature sensor 20s is used for the upper surface and the lower surface of the heat resistor tor, respectively, to measure the magnitude of heat flux discharged from the body surface of the living body 90, while the temperature sensor 20s measures an epidermis temperature Ts. As the temperature sensors 20u and 20s, a well-known thermistor, a thermopile using a thermocouple, an ultrasonic thermometer utilizing the change in sound velocity according to the temperature, an infrared temperature sensor or another optical thermometer utilizing the change in a light absorption rate according to the temperature, or the like is used, for example.

The blood flow sensor 30 is a device which is arranged near the heat flux sensor 20 and measures the blood flow rate of the body surface of the living body 90. As such a blood flow sensor 30, a laser Doppler blood flowmeter or another optical blood flow sensor which measures a blood flow rate in a subcutaneous tissue by irradiating a skin with a laser or an ultrasonic blood flowmeter is used, for example.

The memory 50 stores a relation between parameters regarding a delay time until the fluctuation in the core temperature of the living body is reflected in the epidermis temperature and a blood flow rate of the body surface.

The parameters relating to the delay time until the fluctuation in the core temperature of the living body is reflected in the epidermis temperature are, specifically, a time constant of the fluctuation in the epidermis temperature with respect to the fluctuation in the core temperature of the living body or a delay time until the fluctuation in the core temperature of the living body is reflected in the epidermis temperature. The relation between the blood flow rate and the time constant or the delay time may be stored in the memory 50 in the form of a table, but may be stored as a function. The relation between the blood flow rate and the time constant or the delay time will be described below.

Further, the memory 50 stores the time-series data of the core temperature which is calculated from the result obtained by the measurement of the heat flux sensor 20, that is, data in which the core temperature is associated with the time at which the core temperature is measured, or, as described below, corrected time-series data in which the time is corrected.

The arithmetic circuit 40 includes a timer unit 42, calculates a core temperature Tc of the living body from the epidermis temperature measured by the temperature sensor 20s and the magnitude of the heat flux measured by the heat flux sensor 20, and generates time-series data of the core temperature Tc. Then, the arithmetic circuit 40 calculates, based on the blood flow rate of the body surface in the vicinity of the heat flux sensor 20 and the relation between the delay time and the blood flow rate stored in the memory 50, a delay time Δt until the fluctuation in the core temperature Tc of the living body is reflected in the epidermis temperature, and corrects the time associated with each core temperature Tc forming the time-series data, based on the delay time Δt.

As described above, the arithmetic circuit 40 including a first calculation unit 41, a timer unit 42, a second calculation unit 43, and a correction unit 44 can be formed from an arithmetic device and a computer program. For example, the first calculation unit 41 calculates the core temperature Tc of the living body from the epidermis temperature Ts measured by the temperature sensor 20s and the magnitude of the heat flux measured by the heat flux sensor 20, and generates time-series data of the core temperature Tc together with the measured time of the core temperature Tc counted by the timer unit 42. Then, the second calculation unit 43 calculates the delay time Δt until the fluctuation in the core temperature Tc of the living body is reflected in the epidermis temperature Ts, based on the blood flow rate of the body surface in the vicinity of the heat flux sensor 20 and the relation between the blood flow rate and the delay time stored in the memory 50. Next, the correction unit 44 corrects the time associated with the core temperature Tc, based on the delay time Δt.

The communication circuit 60 is an I/F circuit which outputs the time-series data of the temperature obtained by the correction of the arithmetic circuit 40 to the outside or outputs an alarm when an error occurs. As such a communication circuit 60, an output circuit to which a USB or other cable can be connected is used in a case where data or the like is output by wire. For example, a wireless communication circuit based on Bluetooth (registered trademark) or the like may be used.

The sheet-shaped base material 80 does not only function as a base for placing the heat flux sensor 20, the blood flow sensor 30, the arithmetic circuit 40, the memory 50, the communication circuit 60, and the battery 70 but also includes wiring (not illustrated) which connects those elements electrically. Considering that the internal body temperature measurement device 1 is placed on the epidermis of the living body, a deformable flexible substrate is desirably used as the sheet-shaped base material 80.

Figure 3:
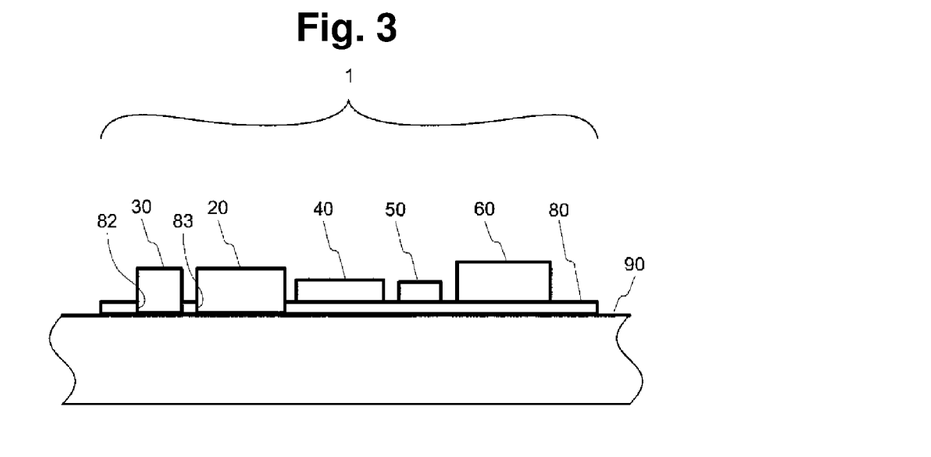
FIG. 3 is a diagram illustrating the configuration of the internal body temperature measurement device according to the first embodiment.

Further, as illustrated in FIG. 3, openings 82 and 83 are provided in a part of the sheet-shaped base material 80, and the heat flux sensor 20 and the blood flow sensor 30 are placed on the base material 80 so as to be in contact with the epidermis of the living body through the openings 82 and 83, respectively.

Figure 4:
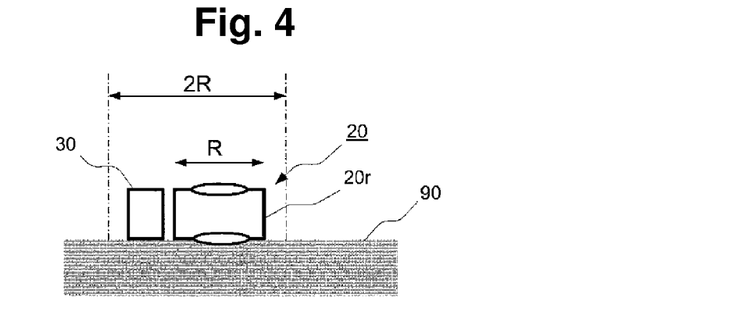
FIG. 4 is a diagram for explaining a positional relation between a heat flux sensor and a blood flow sensor in the internal body temperature measurement device according to the first embodiment.

If the heat resistor 20r of the heat flux sensor 20 is formed, for example, in a disc shape, a region of about twice a diameter R of the heat resistor 20r affects the measurement of the core temperature Tc. Therefore, in order to measure the blood flow rate of the body surface in the vicinity of the heat flux sensor 20 with the blood flow sensor 30, as illustrated in FIG. 4, the blood flow sensor 30 is installed within the region of twice the diameter R of the heat resistor 20r of the heat flux sensor 20, that is, about a diameter 2R around the heat resistor 20r in plan view. One or multiple blood flow sensors 30 can be also provided in one heat flux sensor 20, but in this embodiment, one blood flow sensor 30 is provided in one heat flux sensor 20.

[Measurement Principle of Internal Body Temperature Measurement Device]

Next, the measurement principle of the internal body temperature measurement device according to this embodiment will be described with reference to FIGS. 5 to 8.

Figure 5:
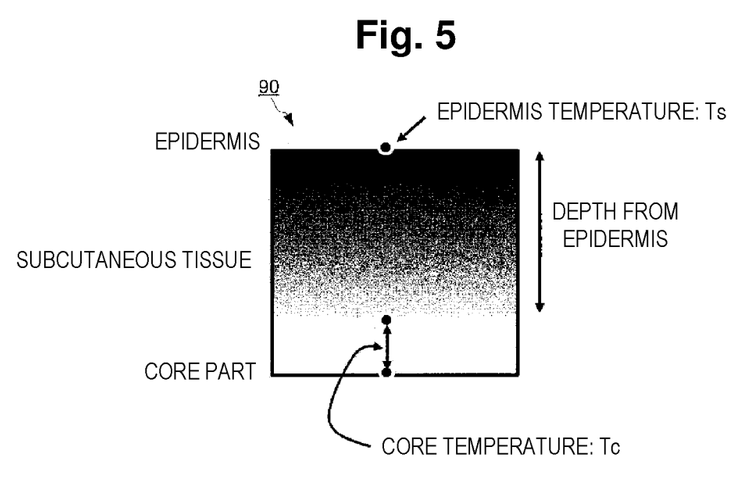
FIG. 5 is a diagram for schematically explaining a temperature distribution of a subcutaneous tissue of a living body.

As illustrated in FIG. 5, the living body 90 has the region of the temperature which is not affected by a change in an outside air temperature or the like beyond a certain depth from the epidermis in a depth direction of the subcutaneous tissue, that is, the core temperature. Typically, the epidermis temperature Ts is lower than the core temperature Tc, and a temperature gradient is generated from the core part toward the epidermis.

Figure 6:
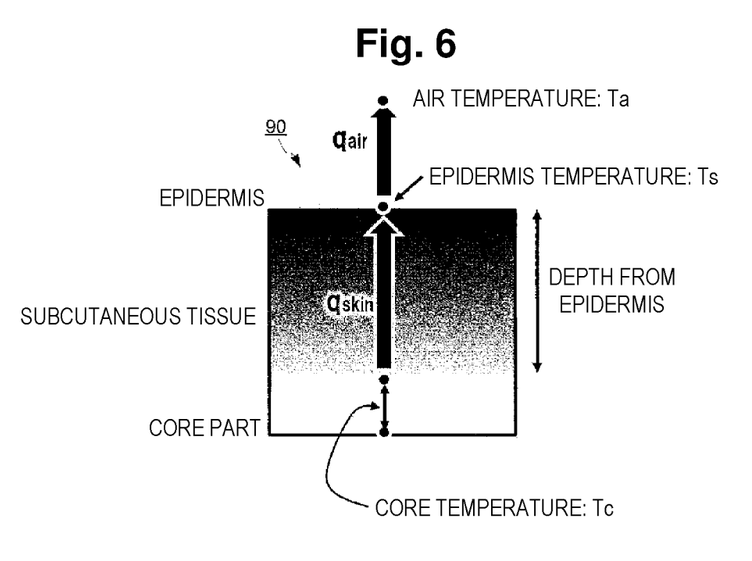
FIG. 6 is a diagram for schematically explaining a heat flux of a subcutaneous tissue of a living body.

Generally, as illustrated in FIG. 6, the time temperature change in the epidermis temperature Ts is expressed as the following Formula (1) from the heat flux $q_{skin}$ from the core part and the heat flux $q_{air}$ into the air.

Formula 1

$$\rho AL \cdot c \cdot \frac{dT_s}{dt} = A(-q_{air} + q_{skin}) \quad (1)$$

Herein, ρ is the density of the subcutaneous tissue, A is the area of the surface through which the heat flux penetrates, c is the heat capacity of the subcutaneous tissue, and L is the depth (distance) frog the epidermis to the temperature region of the core temperature.

The heat flux qair from the epidermis into the air and the heat flux qskin from the core part to the epidermis are expressed as the following Formula (2) by using a proportional constant h (including a thermal radiation coefficient, a thermal transpiration coefficient, and a thermal transfer coefficient into the air) and a thermal conductivity k of the subcutaneous tissue, respectively.

Formula 2

$$q_{air} = h(T_s - T_a), \; q_{skin} = \frac{k}{L}(T_c - T_s), \quad (2)$$

When these formulas are put into Formula (1), the following Formula (3) is obtained.

Formula 3

$$\frac{dT_s}{dt} = -\frac{hL+k}{\rho L^2 c} T_s + \frac{hL \cdot T_a + k \cdot T_c}{\rho L^2 c} \quad (3)$$

In Formula (3), the epidermis temperature Ts has a time constant $\tau = (\rho L^2 c)/(hL+k)$, and thus, it is found that the time until the core temperature Tc is reflected on the epidermis temperature Ts is proportional to the square of the depth L from the epidermis to the temperature region of the core temperature.

Figure 7:
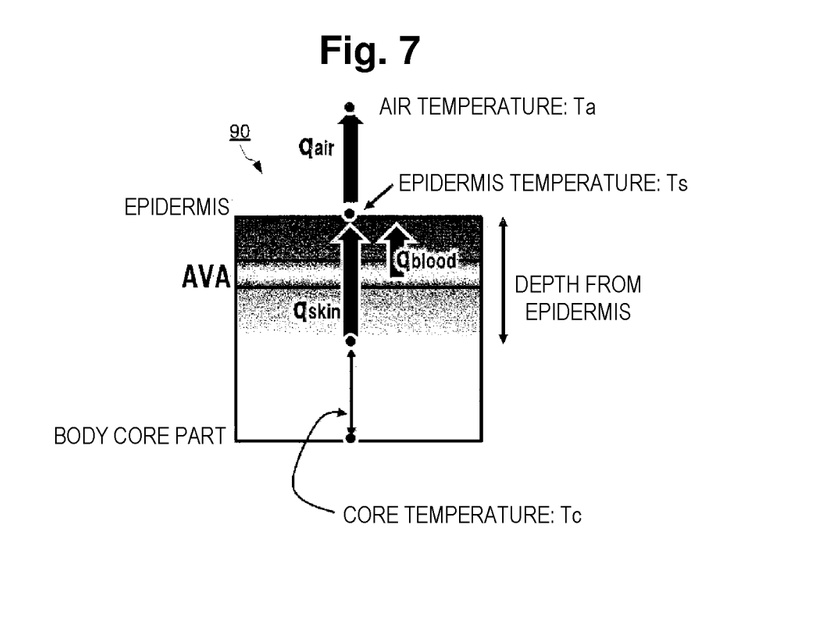
FIG. 7 is a diagram for schematically explaining a relation between a heat flux of a subcutaneous tissue of a living body and a blood flow.
Figure 8:
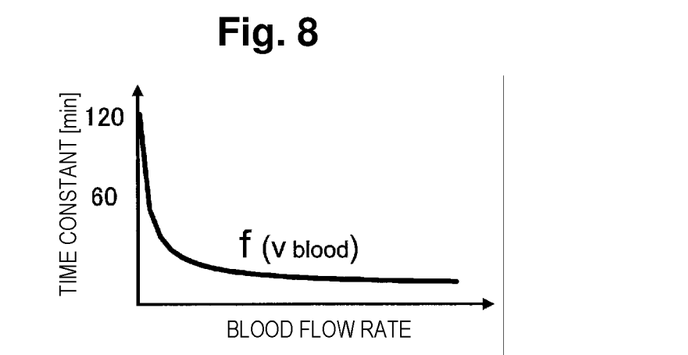
FIG. 8 is a diagram for explaining a relation between a blood flow rate and a time constant of a fluctuation of an epidermis temperature with respect to a fluctuation of a core temperature of a living body.

As described above, it is known that the apparent depth L from the epidermis to the temperature region of the core temperature depends on the blood flow rate (see FIG. 15), and in the living body 90, the apparent depth from the epidermis to the temperature region of the core temperature changes from time to time by the blood flow. In order to model this, when the heat flux $q_{blood}$ from the blood vessel is newly defined as illustrated in FIG. 7, added to Formula (1), and solved similarly, the blood flow rate and the time constant τ have a relation represented in FIG. 8. In this way, the change in the time constant τ becomes the function of the change in the blood flow rate.

As described above, when the depth L from the epidermis to the temperature region of the core temperature changes, the time constant τ changes, and when the blood flow rate changes, the time constant τ changes. From this point, it is known that the apparent depth L from the epidermis to the temperature region of the core temperature is changed along with the change in the blood flow rate.

Incidentally, in a case where the heat flux sensor 20 is used, the magnitude of the heat flux $q_r$ penetrating the heat resistor 20r (the heat flux $q_r$ corresponds to the heat flux $q_{air}$ into the air in FIG. 6 or 7) can be obtained from a difference ΔT between an air temperature Ta and the epidermis temperature Ts measured by two temperature sensors 20u and 20s, and a thermal conductivity λ and a thickness $L_r$ of the heat resistor 20r.

Assuming that the magnitude of the heat flux penetrating the subcutaneous tissue from the core part toward the epidermis is equal to the magnitude of the heat flux penetrating the heat resistor 20r, the first calculation unit 41 (see FIG. 1) of the arithmetic circuit 40 can calculate the core temperature Tc from the heat resistance Rx of the subcutaneous tissue, the heat resistance Rr of the heat resistor 20r, the epidermis temperature Ts, and the air temperature Ta on the basis of the following Formula (4).

[Formula 4]
$$Tc = Ts + \frac{Rx}{Rr}(Ts - Ta) \quad (4)$$

Measurement Method of Internal Body Temperature Measurement Device

Figure 9:
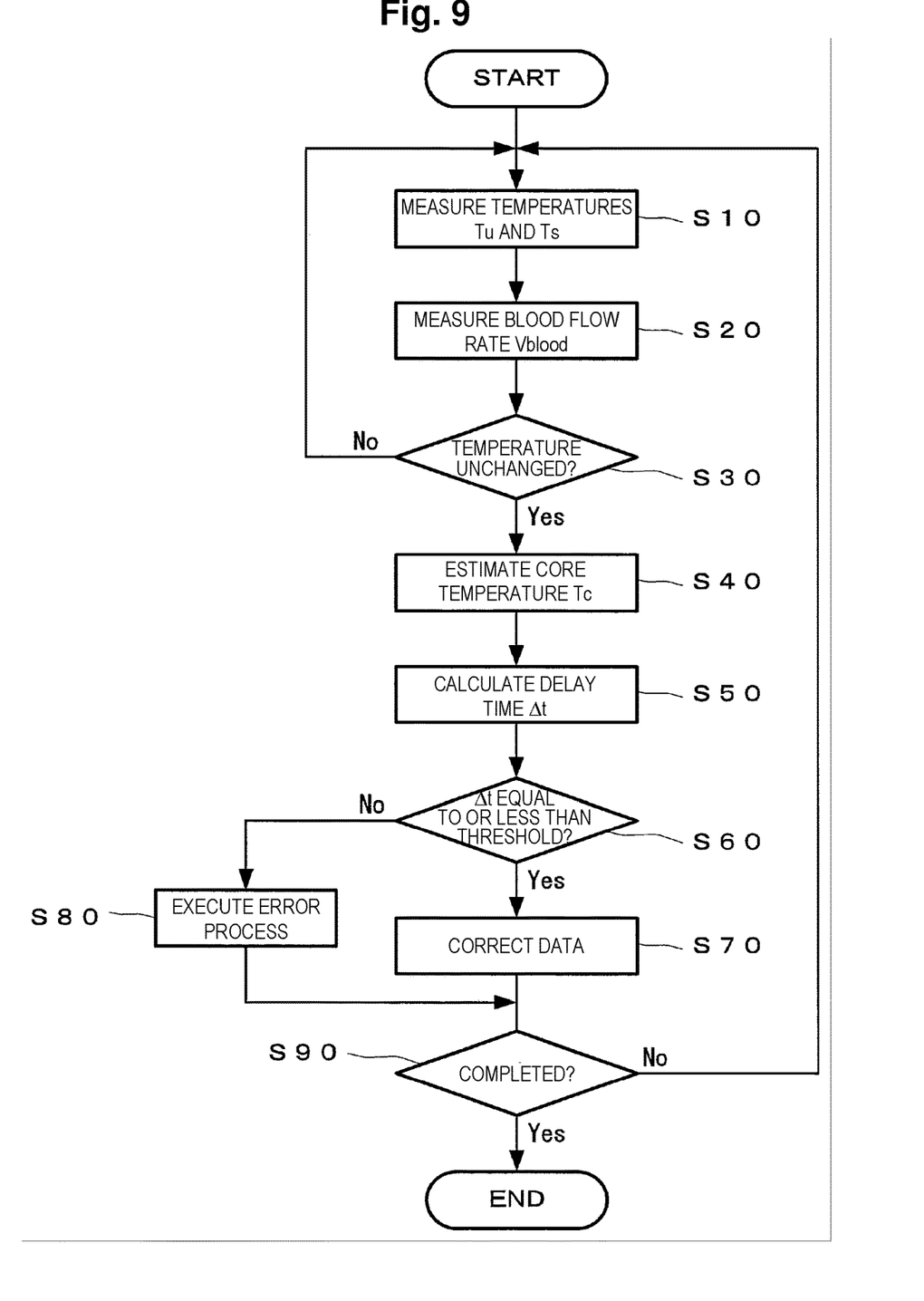
FIG. 9 is a flowchart for explaining an operation of the internal body temperature measurement device according to the first embodiment.

Next, the operation of the internal body temperature measurement device according to this embodiment will be described with reference to FIG. 9.

Incidentally, the relational expression f(vblood) or the table representing the previously prepared relation f(vblood) (see FIG. 8) between the blood flow rate and the time constant τ is stored in the memory 50.

First, the temperature is measured by using two temperature sensors 20u and 20s of the heat flux sensor 20 (step S10). Further, the blood flow rate of the body surface is measured by using the blood flow sensor 30 (step S20). These operations are repeated a plurality of times to determine whether or not the fluctuation of the air temperature Ta and the epidermis temperature Ts falls within a predetermined range (step S30). When the fluctuation does not fall within the predetermined range (step S30: No), it is determined that the heat flux is not in the steady state, the procedure returns to step S10, and steps S10 to S30 are repeated.

On the other hand, when the fluctuation of the air temperature Ta and the epidermis temperature Ts falls within the predetermined range (step S30: Yes), it is determined that the heat flux is in the steady state, the core temperature Tc is estimated from the epidermis temperature Ts and the air temperature Ta (step S40), and a delay time Δt is calculated (step S50). In the calculation of the delay time Δt (step S50), the time constant t corresponding to the blood flow rate of the body surface detected by the blood flow sensor 30 is obtained with reference to the relation f(vblood) between the blood flow rate and the time constant τ stored in the memory 50, and the delay time Δt is calculated. The delay time Δt is obtained from the following Formula (5) by using the previously determined constant α.

$$\Delta t = \alpha \times f(vblood) \quad (5)$$

Herein, the constant α can be calculated from a phase delay in the frequency response obtained from the time constant τ.

After the delay time Δt is calculated, the delay time Δt is compared with a predetermined threshold (step S60). In a case where the calculated delay time Δt is larger than the threshold (step S60: No), a predetermined error process such as an alarm notification is executed (step S80). In that case (step S60: No), the change in the core temperature cannot be followed, and the change in the core temperature Tc as well as the core temperature Tc is not observable. Thus, it is determined that the estimation of the core temperature is impossible.

On the other hand, in a case where the calculated delay time Δt is equal to or less than the threshold (step S60: Yes), the time-series data is corrected by temporally shifting the time of the core temperature Tc estimated at that time by the delay time Δt (step S70).

Until the indication of completion is given (step S90: Yes), the above steps are repeated.

Figure 10:
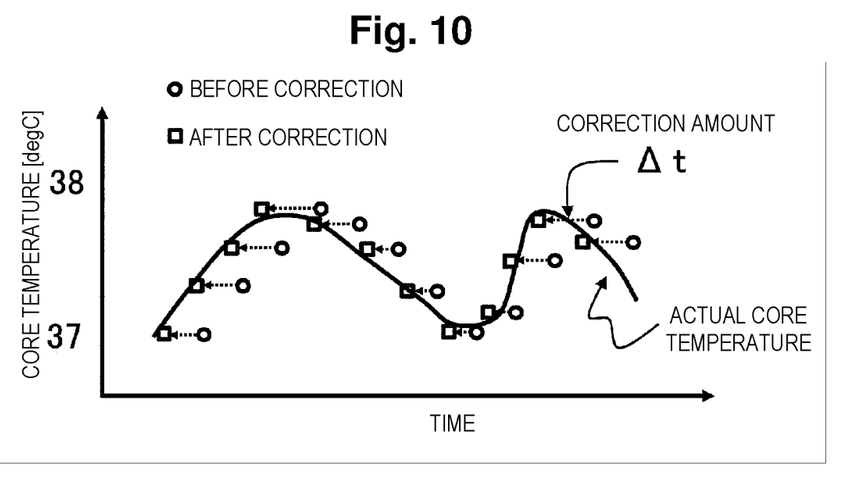
FIG. 10 is a diagram for explaining correction of time-series data of a core temperature based on a delay time.

One example of the time-series data of the core temperature Tc obtained by the above correction is illustrated in FIG. 10. In FIG. 10, a solid line indicates the actual core temperature, and ○ mark and □ mark indicate the estimated core temperature before correction and the core temperature after correction, respectively. In a case where the delay time Δt associated with the change in the blood flow rate is not taken into consideration (○ mark), a deviation is generated on a time base in comparison with the actual core temperature Tc.

On the other hand, in the time-series data obtained by the correction using the delay time Δt calculated according to the blood flow rate, the deviation on the time base from the actual core temperature Tc is reduced. Therefore, according to the internal body temperature measurement device according to this embodiment, the fluctuation of the core temperature can be grasped more accurately.

Figure 11:
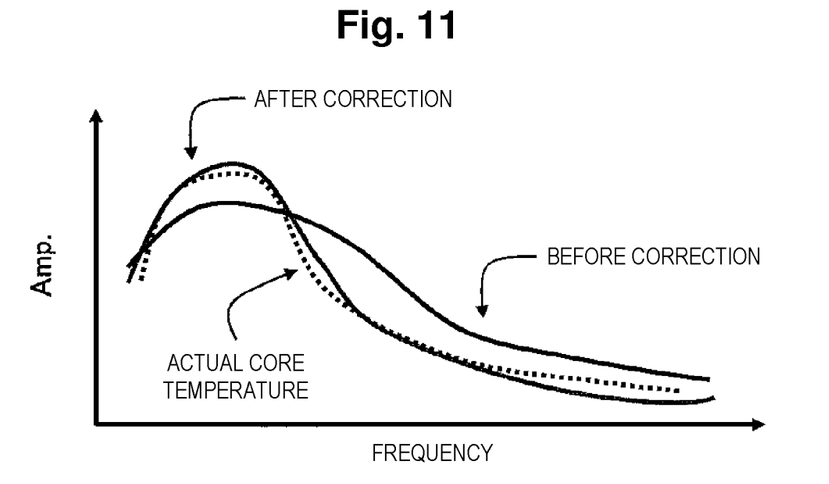
FIG. 11 is a diagram for explaining frequency information of the fluctuation of the core temperature restored by the correction of data based on the delay time.

For example, in the internal body temperature measurement device according to this embodiment, the calculated correction amount, that is, the delay time Δt is fluctuated depending on the blood flow rate. Thus, as illustrated in FIG. 1i, the frequency information of the fluctuation of the core temperature Tc lost in the past can also be restored from the corrected time-series data of the core temperature Tc. Accordingly, the fluctuation of the core temperature Tc as the internal body rhythm can be grasped more accurately.

Second Embodiment

Figure 12:
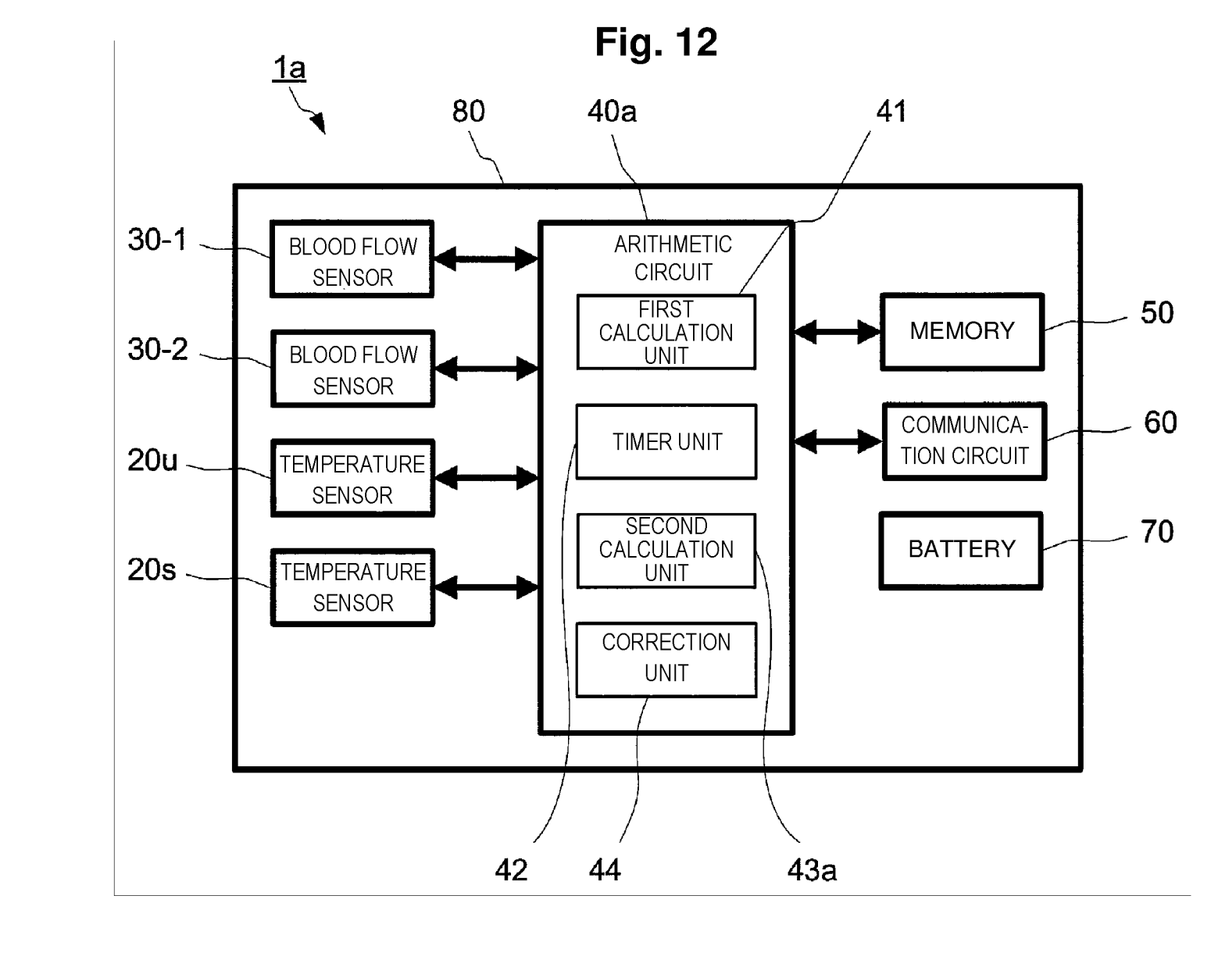
FIG. 12 is a diagram illustrating a configuration of an internal body temperature measurement device according to a second embodiment of the present invention.

Next, a second embodiment of the present invention will be described with reference to FIGS. 12 and 13. Incidentally, the same reference symbols are used for the components common to the above-described internal body temperature measurement device 1 according to the first embodiment, and the detailed description thereof will be omitted.

The internal body temperature measurement device 1 according to the first embodiment uses one blood flow sensor 30 with respect to one heat flux sensor 20. However, the internal body temperature measurement device according to the second embodiment 1a includes a plurality of blood flow sensors with respect to one heat flux sensor 20. Specifically, as illustrated in FIG. 12, the internal body temperature measurement device according to the second embodiment 1a includes, on the sheet-shaped base material 80, the heat flux sensor 20 which includes two temperature sensors 20u and 20s, two blood flow sensors 30-1 and 30-2, an arithmetic circuit 40a, the memory 50, the communication circuit 6o which functions as the I/F circuit with the outside, and the battery 70 which supplies power to the arithmetic circuit 40a, the communication circuit 60, or the like.

The internal body temperature measurement device 1a according to this embodiment includes two blood flow sensors 30-1 and 30-2 with respect to one heat flux sensor 20. Accordingly, the arithmetic circuit 40a is configured such that the second calculation unit 43a obtains the average value of respective blood flow rates measured by two blood flow sensors 30-1 and 30-2 as the representative value of the blood flow rates and obtains the time constant or the delay time Δt corresponding to the average value of the blood flow rates by using the relation stored in the memory 50.

Two blood flow sensors 30-1 and 30-2 are arranged in the vicinity of the heat resistor 20r of the heat flux sensor 20. At this time, when the effect of the region of about twice the diameter R of the heat resistor 20r on the measurement of the core temperature Tc is taken into consideration, as illustrated in FIG. 13, two blood flow sensors 30-1 and 30-2 are installed within the region of twice the diameter R of the heat resistor 20r of the heat flux sensor 20, that is, about the diameter 2R around the heat resistor 20r in plan view.

Figure 13:
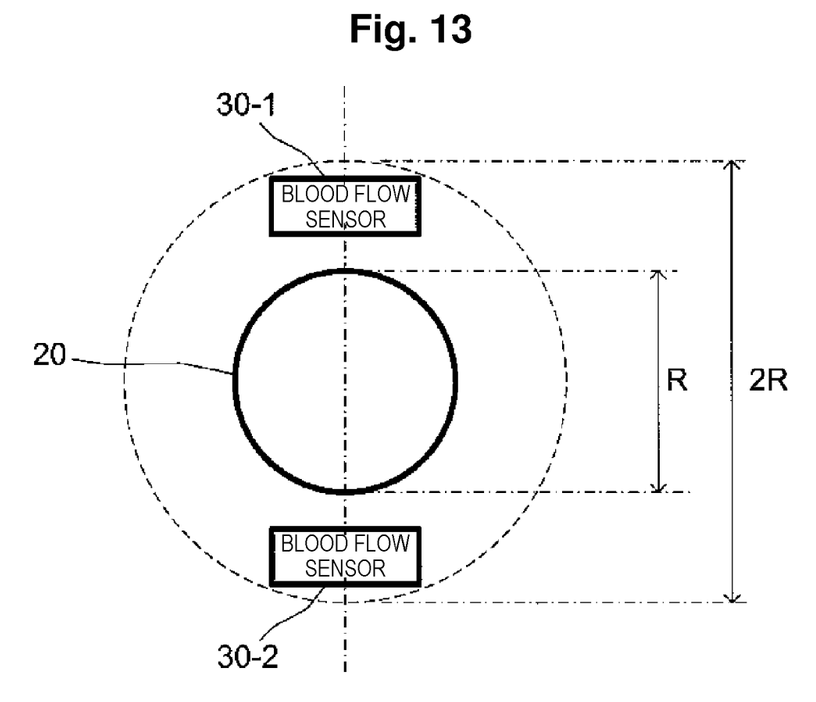
FIG. 13 is a diagram for explaining a positional relation between a heat flux sensor and a blood flow sensor in the internal body temperature measurement device according to the second embodiment of the present invention.

Incidentally, in this embodiment, as illustrated in FIG. 13, two blood flow sensors 30-1 and 30-2 are arranged at positions of a line object across the heat resistor 20r of the heat flux sensor 20 in plan view.

As described above, the blood flow rate in the vicinity of the heat flux sensor can be measured accurately by using a plurality of blood flow sensors. Thus, the estimation accuracy of the delay time Δt is improved, and the fluctuation of the core temperature can be grasped more accurately.

Figure 14:
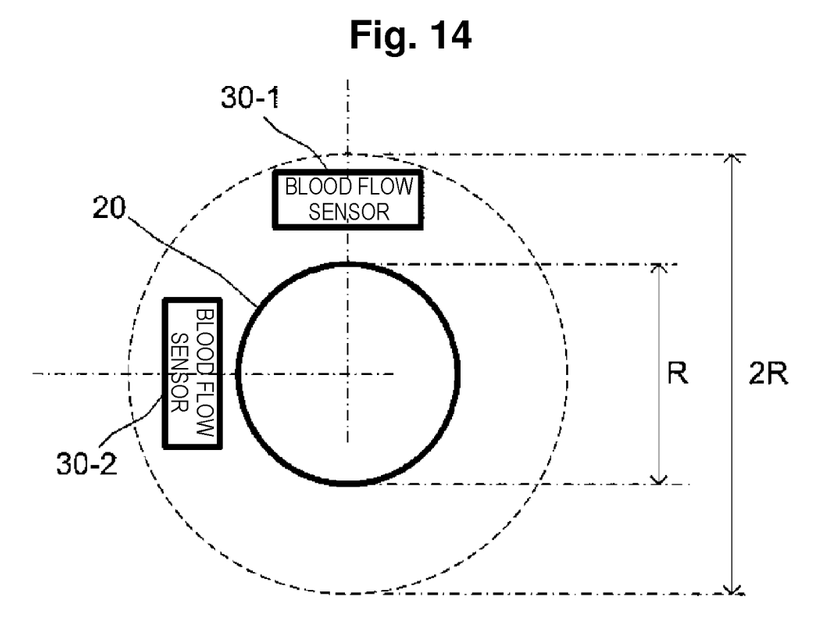
FIG. 14 is a diagram for explaining a modification of the positional relation between the heat flux sensor and the blood flow sensor in the internal body temperature measurement device according to the second embodiment of the present invention.

Incidentally, in this embodiment, two blood flow sensors are arranged at positions of a line object across the heat resistor 20r of the heat flux sensor 20 in plan view. However, the present invention is not limited thereto. For example, as illustrated in FIG. 14, in plan view, two blood flow sensors 30-1 and 30-2 may be arranged to be positioned at two lines passing through the center of the heat resistor 20r of the heat flux sensor 20 and crossing each other at right angles.

In this embodiment, two blood flow sensors 30-1 and 30-2 are used. However, of course, three or more blood flow sensors may be used.

Further, as the representative value of respective blood flow rates measured by the plurality of blood flow sensors, the average value of the blood flow rates can be used. However, instead of the average value, a maximum value or a minimum value may be used, and in addition, in the case of using three or more blood flow sensors, a median value or the like may be used.

REFERENCE SIGNS LIST 1, 1a Internal body temperature measurement device
20 Heat flux sensor
20u, 20s Temperature sensor
20r Heat resistor
30 Blood flow sensor
40 Arithmetic circuit
50 Memory
60 Communication circuit
70 Battery
80 Base material
90 Living body.

The invention claimed is:

1. An internal body temperature measurement device comprising:
a temperature sensor configured to measure an epidermis temperature of a living body;
a heat flux sensor configured to measure a magnitude of a heat flux discharged from a body surface of the living body;
a blood flow sensor configured to measure a blood flow rate in a vicinity of the heat flux sensor;
a non-transitory memory which stores a relation between a plurality of different blood flow rates of the living body and a parameter, the parameter defining a respective delay time until a fluctuation of a core temperature of the living body is reflected on the epidermis temperature of the living body for each of the plurality of different blood flow rates; and
an arithmetic circuit configured to:
calculate the core temperature of the living body from the epidermis temperature and the magnitude of the heat flux;
calculate a delay time corresponding to the epidermis temperature measured by the temperature sensor by correlating the blood flow rate measured by the blood flow sensor in the vicinity of the heat flux sensor and the relation between the plurality of different blood flow rates and the parameter stored in non-transitory memory; and
correct a time corresponding to the core temperature of the living body based on the delay time, wherein correcting the time corresponding to the core temperature of the living body based on the delay time comprises correcting the time corresponding to the core temperature of the living body based on the delay time that is less than a predetermined threshold.

2. The internal body temperature measurement device according to claim 1, wherein the arithmetic circuit includes:
a first calculator which calculates the core temperature of the living body from the epidermis temperature and the magnitude of the heat flux,
a second calculator which calculates the delay time based on of the blood flow rate in the vicinity of the heat flux sensor and the relation stored in the non-transitory memory, and
a corrector which corrects the time corresponding to the core temperature of the living body based on the delay time.

3. The internal body temperature measurement device according to claim 1, wherein the parameter is a time constant of a fluctuation of the epidermis temperature with respect to the fluctuation of the core temperature of the living body or the delay time.

4. The internal body temperature measurement device according to claim 1, further comprising:
a first blood flow sensor and a second blood flow sensor, wherein the arithmetic circuit obtains a representative value of a first blood flow rate measured by the first blood flow sensor and a second blood flow rate measured by the second blood flow sensor, and wherein the arithmetic circuit calculates the delay time based on the representative value and the relation stored in the non-transitory memory.

5. The internal body temperature measurement device according to claim 1, wherein the core temperature is a temperature of a core of the living body, and wherein the core of the living body is separated from the body surface by subcutaneous tissue.

6. The internal body temperature measurement device according to claim 1, wherein the non-transitory memory which stores the relation between the plurality of different blood flow rates and the parameter stores the relation as a table correlating each of the plurality of different blood flow rates with the respective delay time.

7. The internal body temperature measurement device according to claim 1, wherein the non-transitory memory which stores the relation between the plurality of different blood flow rates and the parameter stores the relation as a function correlating each of the plurality of different blood flow rates with the respective delay time, wherein blood flow rate is a variable of the function.

8. An internal body temperature measurement method comprising:
   measuring, by a temperature sensor, an epidermis temperature of a living body;
   measuring, by a heat flux sensor, a magnitude of a heat flux discharged from a body surface of the living body;
   measuring, by a blood flow sensor, a blood flow rate of the living body; and
   calculating a core temperature of the living body from the epidermis temperature and the magnitude of the heat flux;
   calculating a delay time corresponding to the epidermis temperature measured by the temperature sensor by correlating the blood flow rate measured by the blood flow sensor and a relation between a plurality of different blood flow rates and a parameter, the parameter defining a respective delay time until a fluctuation of the core temperature of the living body is reflected on the epidermis temperature of the living body with each of the plurality of different blood flow rates; and
   correcting a time corresponding to the core temperature of the living body based on the delay time, wherein correcting the time corresponding to the core temperature of the living body based on the delay time comprises correcting the time corresponding to the core temperature of the living body based on the delay time that is less than a predetermined threshold.

9. The method according to claim 8, wherein the relation between the blood flow rate and the parameter was stored prior to calculating the delay time.

10. The method according to claim 8, wherein the parameter is a time constant of a fluctuation of the epidermis temperature with respect to the fluctuation of the core temperature of the living body or the delay time.

11. The method according to claim 8, wherein the core temperature is a temperature of a core of the living body, and wherein the core of the living body is separated from the body surface by subcutaneous tissue.

12. The method according to claim 8, wherein the relation is stored as a table correlating each of the plurality of different blood flow rates with the respective delay time.

13. The method according to claim 8, wherein the relation is stored as a function correlating each of the plurality of different blood flow rates with the respective delay time, wherein blood flow rate is a variable of the function.

* * * * *